United States Patent
Ensign et al.

(10) Patent No.: US 8,100,948 B2
(45) Date of Patent: Jan. 24, 2012

(54) LOW PROFILE PEDICLE SCREW ASSEMBLY

(75) Inventors: Michael D. Ensign, Salt Lake City, UT (US); David T. Hawkes, Pleasant Grove, UT (US)

(73) Assignee: K2M, Inc., Leesburg, VA (US)

( * ) Notice: Subject to any disclaimer, the term of this patent is extended or adjusted under 35 U.S.C. 154(b) by 921 days.

(21) Appl. No.: 12/116,751

(22) Filed: May 7, 2008

(65) Prior Publication Data
US 2008/0243193 A1  Oct. 2, 2008

Related U.S. Application Data

(63) Continuation-in-part of application No. 11/440,549, filed on May 25, 2006.

(60) Provisional application No. 60/928,150, filed on May 7, 2007, provisional application No. 60/684,695, filed on May 25, 2005.

(51) Int. Cl.
*A61B 17/70* (2006.01)

(52) U.S. Cl. ........................................ 606/267; 606/305

(58) Field of Classification Search ................ 606/86 A, 606/104, 60, 246–279, 300, 305, 306, 319, 606/328, 331
See application file for complete search history.

(56) References Cited

U.S. PATENT DOCUMENTS

| | | | |
|---|---|---|---|
| 5,468,241 A | 11/1995 | Metz-Stavenhagen et al. | |
| 5,683,392 A | 11/1997 | Richelsoph et al. | |
| 5,738,685 A | 4/1998 | Halm et al. | |
| 5,817,094 A | 10/1998 | Errico et al. | |
| 5,876,403 A | 3/1999 | Shitoto | |
| 5,964,760 A * | 10/1999 | Richelsoph | 606/279 |

(Continued)

OTHER PUBLICATIONS

Non-Final Office Action dated Mar. 17, 2009 for U.S. Appl. No. 11/440,549.
Response to Non-Final Office Action dated Mar. 17, 2009 for U.S. Appl. No. 11/440,549.
Final Office Action dated Dec. 10, 2009 for U.S. Appl. No. 11/440,549.
Response to Final Office Aciton dated Dec. 10, 2009 for U.S. Appl. No. 11/440,549.
Non-Final Office Action dated May 20, 2010 for U.S. Appl. No. 11/440,549.
Response to Non-Final Office Action dated May 20, 2010 for U.S. Appl. No. 11/440,549.

*Primary Examiner* — Eduardo C Robert
*Assistant Examiner* — Lynnsy Schneider
(74) *Attorney, Agent, or Firm* — Carter, DeLuca, Farrell & Schmidt, LLP

(57) ABSTRACT

A pedicle screw and rod assembly is provided which has a low profile in the final position. The pedicle screw includes a screw having a threaded portion and a head portion. A tulip body is positioned on the head portion of the screw. A tulip saddle is coupled to the tulip body and positioned to retain the tulip assembly on the pedicle screw. Wedge members are inserted in between the tulip body and the tulip saddle, causing the saddle to compress and thereby retain a rod within the tulip assembly. Colored wedge members alert a surgeon as to whether the system is in a locked or unlocked state. The top of the tulip assembly is approximately equal in height to, or lower than the rod itself. This provides a low profile pedicle screw and rod assembly since the rod itself will be the uppermost member of the completed assembly.

25 Claims, 12 Drawing Sheets

U.S. PATENT DOCUMENTS

| | | |
|---|---|---|
| 5,989,250 A | 11/1999 | Wagner et al. |
| 6,113,601 A | 9/2000 | Tartar |
| 6,273,888 B1 | 8/2001 | Justis |
| 6,355,040 B1 | 3/2002 | Richelsoph et al. |
| RE37,665 E | 4/2002 | Ralph et al. |
| 6,402,752 B2 | 6/2002 | Schaffler-Wachter et al. |
| 6,416,515 B1 | 7/2002 | Wagner |
| 6,440,137 B1 | 8/2002 | Horvath et al. |
| 6,740,086 B2 | 5/2004 | Richelsoph |
| 7,090,674 B2 | 8/2006 | Doubler et al. |
| 7,951,172 B2 * | 5/2011 | Chao et al. .................. 606/265 |
| 2003/0167058 A1 | 9/2003 | Shluzas |
| 2005/0137594 A1 | 6/2005 | Doubler et al. |
| 2005/0154391 A1 | 7/2005 | Doherty et al. |
| 2006/0004357 A1 | 1/2006 | Lee et al. |
| 2006/0025768 A1 | 2/2006 | Iott et al. |
| 2006/0074418 A1 | 4/2006 | Jackson |
| 2006/0155278 A1 | 7/2006 | Warnick |
| 2006/0229615 A1 * | 10/2006 | Abdou ........................ 606/61 |
| 2008/0045963 A1 * | 2/2008 | Abdou ........................ 606/73 |

* cited by examiner

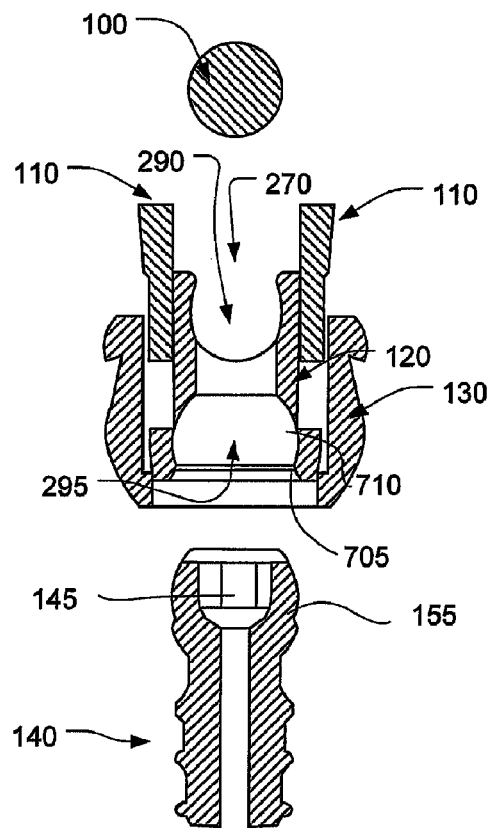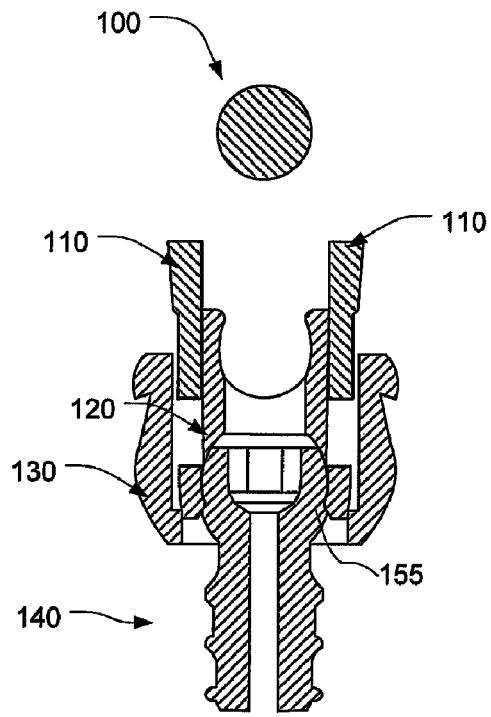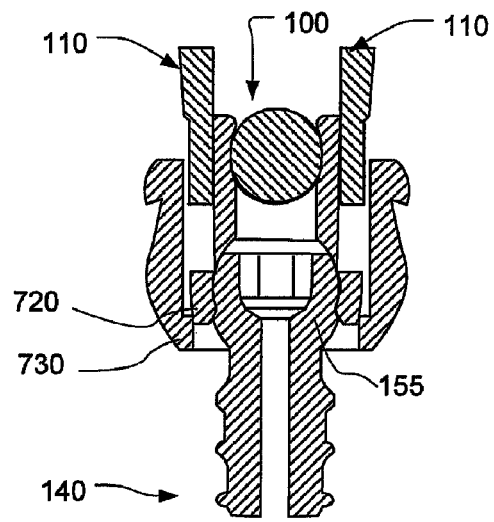
Fig. 7A
Fig. 7B
Fig. 7C

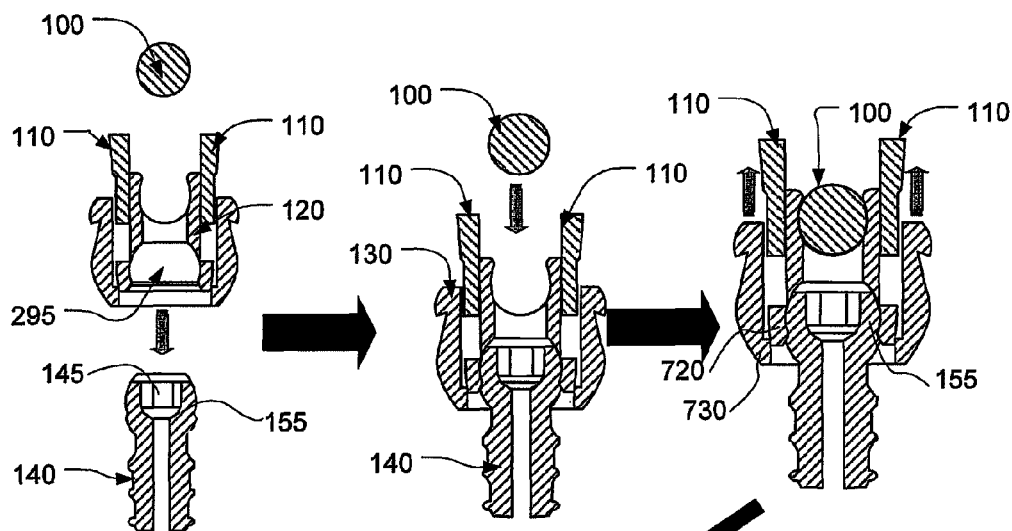
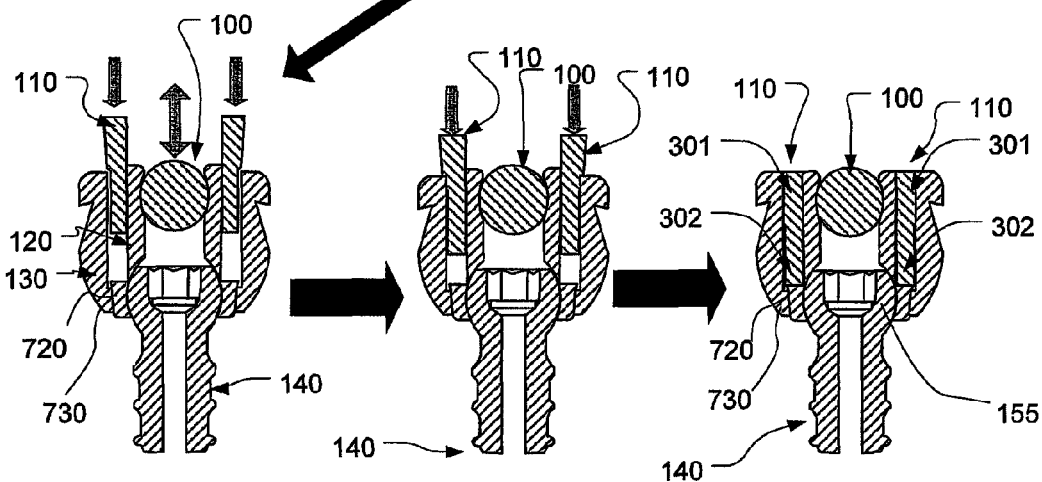
Fig. 12A  Fig. 12B  Fig. 12C
Fig. 12D  Fig. 12E  Fig. 12F

LOW PROFILE PEDICLE SCREW ASSEMBLY

RELATED APPLICATIONS

This application is a continuation-in-part application of U.S. patent Ser. No. 11/440,549 filed May 25, 2006 and titled "Low Profile Pedicle Screw and Rod Assembly", which application claims the benefit under 35 U.S.C. §119(e) of U.S. Provisional Patent Application No. 60/684,695 filed May 25, 2005 and also titled "Low Profile Pedicle Screw and Rod Assembly." Furthermore, the present application claims the benefit under 35 U.S.C. §119(e) of U.S. Provisional Patent Application No. 60/928,150 filed May 7, 2007, titled "Low Rider Pedicle Screw System Including Restraint Features." The above-mentioned applications are incorporated herein by reference in their entireties.

TECHNICAL FIELD

The present exemplary system and method relates to medical devices. More particularly, the present exemplary system and method relates to pedicle screw and rod combinations that have a low profile when finally assembled.

BACKGROUND

Various devices for internal fixation of bone segments in the human or animal body are known in the art. One type of system is a pedicle screw system, which may be used as an adjunct to spinal fusion surgery, and which provides a means of gripping a spinal segment. This is particularly used within the fields of orthopedic surgery and neurosurgery, in which spinal implants and rods hold vertebral members in position relative to one another.

A conventional pedicle screw system comprises a pedicle screw and a rod-receiving device. Two such systems are inserted into respective vertebrae and adjusted to distract and/or stabilize a spinal column, for instance during an operation to correct a herniated disk. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

Although conventional prior art pedicle screw systems exist, they lack features that enhance and/or benefit newer, minimally invasive surgery (MIS) techniques that are more commonly being used for spinal surgeries. It has been suggested that one possible advantage of an MIS approach is that it can increase a patient's rate of recovery.

Conventional pedicle screw systems and even more recently designed pedicle screw systems have several drawbacks. Some of these pedicle screw systems are rather large and bulky, which may result in more tissue damage in and around the surgical site when the pedicle screw system is installed during surgery. Traditional pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

SUMMARY

In one of many possible embodiments, a pedicle screw and rod assembly is provided which has a low profile in the final assembled position. The pedicle screw includes a screw having a threaded portion and a head portion. A tulip body (the body) is positioned on the head portion of the screw. A tulip saddle (the saddle) is coupled to the body and is configured to retain the head portion of the pedicle screw secured to the body and saddle. Wedge members are configured to be inserted between the body and the saddle; the varying profile of the wedge members, when inserted, compress the saddle and secure a rod within a rod-receiving channel of the saddle. The top of the wedge members, saddle and body are relatively flush and are approximately equal to, or lower than the uppermost portion of the rod. This provides a low profile pedicle screw and rod assembly since the rod itself will be at least part of the uppermost member of the completed assembly.

According to one exemplary embodiment, the saddle is snapped onto the head portion of a pedicle screw, where it retains the pedicle screw in a partially secured state. In addition, to the saddle coupling the head of the pedicle screw, the body acts to further aid in securement of the pedicle screw. The saddle is coupled to the body, preventing separation of the two components; according to one exemplary embodiment, the saddle is configured with slots allowing pins to secure the saddle to the body, which is configured with corresponding slots or pin-receiving components. According to one exemplary embodiment, the tulip saddle and the tulip body may be coupled together by pins. The body and the saddle, in conjunction, secure the head of a pedicle screw in two positions. A first position in which the head is secured from release, while still free to rotate and pivot, and a second position in which the head is fully secured; that is, an angular position is locked securing the tulip assembly and the pedicle screw at a desired angle.

According to yet another exemplary embodiment, once the saddle and body are coupled, a rod may be snapped into a rod-receiving channel within the saddle. The rod may be snapped in and out as desired, and may translate longitudinally as well. Wedge members are configured to be coupled to at least one side of the tulip saddle, and according to one exemplary embodiment, the saddle is configured to be mated with two wedge members, one on each side. Corresponding intrusions and protrusions on the wedge members and the tulip saddle are configured to retain the wedge members in several positions. According to one exemplary embodiment, the wedge members are of a varying profile, a first narrower portion and a second wider portion. As the wedge member is inserted between the tulip saddle and the tulip body, the wedge member may be coupled by the previously mentioned intrusions and protrusions to the saddle, while not yet acting to compress the saddle. As the wedge members are inserted to a first securing position, according to one exemplary embodiment, the saddle is compressed and partially secures the rod; the rod is free to translate within the rod-receiving channel of the saddle, but is prevented from snapping in and out of the channel. In another wedge member position, fully inserted, the wedge members, the tulip saddle, and the tulip body, sit flush with one another and sit even with or lower than the top of the rod. In this second fully inserted position, the wedge members compress the tulip saddle and thereby secure the rod within the channel completely, preventing the rod from movement. According to one exemplary embodiment, the wedge members are colored in such a way so as to assist the surgeon in determining the state of the tulip assembly.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

FIG. 7A is a cross sectional view illustrating an assembled tulip assembly comprising wedge members, a tulip body, and a tulip saddle, prior to attachment to a pedicle screw and receipt of a rod, according to one exemplary embodiment.

FIG. 7B is a cross section view illustrating a tulip assembly coupled to a pedicle screw in a first, partially secured, state, prior to receipt of a rod, according to one exemplary embodiment.

FIG. 7C is a cross sectional view illustrating a tulip assembly coupled to pedicle screw in a first, partially secured state, and a rod snapped in place in an initial unsecured state, according to one exemplary embodiment.

FIGS. 12A-12F illustrate an exemplary process of securing a tulip assembly to a pedicle screw and subsequent securement of a rod, according to one exemplary embodiment.

Figure 1:
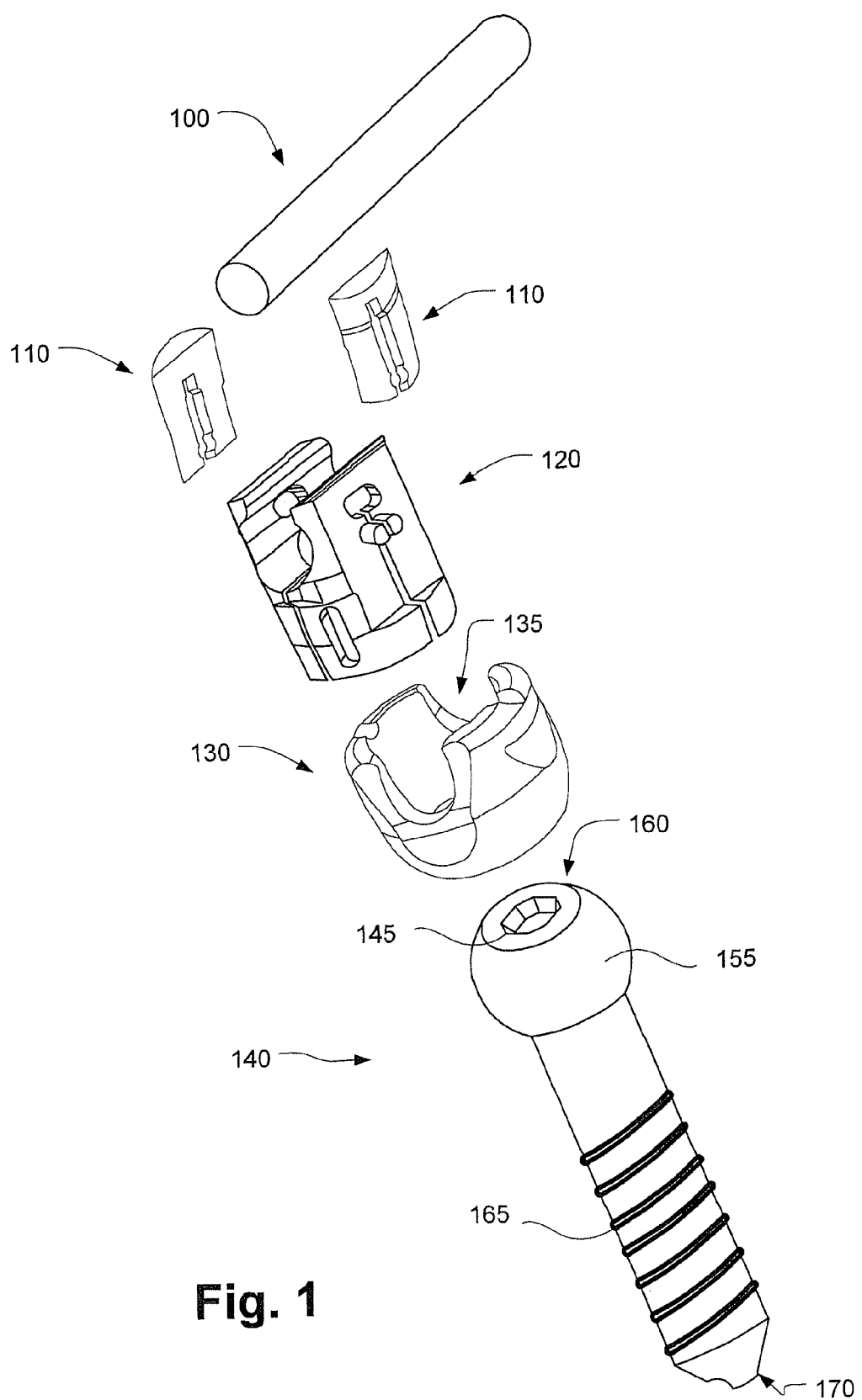
FIG. 1 is an exploded view showing several of the components of a pedicle screw assembly, according to one exemplary embodiment.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification provides a number of exemplary connection members and methods that can be used for any number of orthopedic rod placement systems. According to the present exemplary system and method, a pedicle screw and rod assembly is provided that has a low profile when in a final assembled position. Specifically, the present exemplary systems and methods provide for a pedicle screw and rod assembly system including a rod retaining member that includes a plurality of compression wedges to fix the rod within the screw assembly. According to one exemplary embodiment, the rod retaining member is approximately equal to, or lower than the rod itself. This provides a low profile pedicle screw and rod assembly since the rod itself will normally be the uppermost member of the fully locked assembly. Further details of the present system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques with minimal tissue damage is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the larger and bulkier tulip assembly. Such an advantageous pedicle screw system may be even more crucial when using MIS techniques because the inter-body spatial boundaries in which the surgeon must work may be quite limited.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

In the following description, certain specific details are set forth in order to provide a thorough understanding of various embodiments of the present percutaneous pedicle screw system. However, one skilled in the relevant art will recognize that the present exemplary system and method may be practiced without one or more of these specific details, or with other methods, components, materials, etc. In other instances, well-known structures associated with pedicle screws have not been shown or described in detail to avoid unnecessarily obscuring descriptions of the embodiments of the systems and methods.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

Throughout the description the term tulip assembly should be understood to mean at least a portion of the system described herein, wherein the system comprises a tulip body (130, FIG. 1), a tulip saddle (120, FIG. 1), wedge members (110, FIG. 1), and pins (not shown) for coupling the tulip saddle and the tulip body.

FIG. 1 illustrates an exploded view of one exemplary embodiment of the present system and method. It is illustrated that the present exemplary system, according to one exemplary embodiment, comprises of a distraction rod (100), at least one wedge member (110), a tulip saddle (120), a tulip body (130), and a pedicle screw (140). The pedicle screw is best illustrated in FIG. 1 as having a proximal end (160) and a distal end (170). The proximal end (160) is configured with a head portion (155) and contains driving features (145). The shaft of the pedicle screw approaching the distal end (170) is configured with a threaded portion (165), wherein the threads (165) are configured to aid in penetrating a bone and securing the pedicle screw (140) within a patient's bone. The pedicle screw (140) may have a tip on the distal end (170) configured to facilitate easier penetration of the bone, and may also be configured to remove material as the bone is penetrated allowing the pedicle screw (140) to be inserted with no pre-drilling. The pedicle screw (140) as described is one exemplary embodiment of a pedicle screw, however many variations of commonly used pedicle screws may be used with the present exemplary system and method described herein. As described in conjunction with subsequent illustrations, the pedicle screw may represent any number of pedicle screws.

A method of using and installing the present system will be described in greater detail below; however, to better understand the structure as shown in FIG. 1 a brief explanation is provided. The present exemplary system secures a tulip assembly to a pedicle screw (140) and secures a rod (100) within the tulip assembly. Where the term "tulip assembly" comprises a tulip body (130), a tulip saddle (120), and at least one wedge member (110), and any additional connecting elements. The tulip body (130) (hereinafter referred to as the body) is a substantially cylindrical or circular member having a bore (135) extending from a top portion to a lower portion. The bore (135) is configured to receive a head portion (155) of a pedicle screw (140). According to one exemplary embodiment, the body (130) captures the head (155) of a pedicle screw (140) and while allowing rotation and angular movement, prevents release of the pedicle screw (140)

According to another exemplary embodiment, as illustrated in FIG. 1, the body (130) is configured to allow the head portion to pass through the bore (135) and be captured by the tulip saddle (120) (hereinafter referred to as the saddle). The body (130), according to one exemplary embodiment, is configured to aid the saddle (120) in fully securing the head (155) of a pedicle screw (140) as well as aid in securement of a rod (100). According to one exemplary embodiment, the saddle (120) and the body (130) are coupled to one another through slots and pins; wherein a pin is inserted through slots in both the body (130) and the saddle (120) and thereby prevents separation of the two. According to an alternative embodiment, the saddle (120) and the body (130) are manufactured as one piece, thereby eliminating the need for coupling members, such as pins and slots, to secure them together. According to various embodiments, the saddle (120) and the body (130) are coupled to one another through various methods including but in no way limited to adhesives, welds, fasteners, and the like.

As illustrated in FIG. 1, and as will be described in greater detail in conjunction with subsequent drawings, a saddle (120) is configured with a lower portion and an upper portion. The lower portion captures the head (155) of a pedicle screw (140) and in conjunction with a body (130) secures the pedicle screw (140) at a desired angle relative to the tulip assembly. According to one exemplary embodiment, as will be delineated in greater detail below, the lower portion of the saddle (120) is configured with expansion slots allowing the saddle (120) to expand and then contract, thereby capturing the head (155) of a pedicle screw (140). Additionally, the upper portion of the saddle (120) is configured to allow a rod (100) to be snapped into place.

The upper portion of the saddle (120), as shown in FIG. 1 according to one exemplary embodiment, is generally a cylindrical shape, however, the outer walls may include a substantially planar portion configured to be mated with two wedge members (110). As shown in the exemplary embodiment illustrated in FIG. 1, the saddle (120) has two substantially planar sides and is configured to be mated with two wedge members (110), however it is conceivable that the saddle (120) may only have one substantially planar portion and be configured to be mated with only one wedge member (110). It is also possible that the saddle (120) may be a polygonal cylindrical tulip shape having multiple sides each configured to receive a wedge member (110). Furthermore, according to one exemplary embodiment, the substantially planar sides of the saddle (120) illustrated in FIG. 1 could be replaced by a stepped surface to perform substantially the same function as the stepped outer surfaces of the wedge members (110), which function will be described in detail below.

As illustrated in FIG. 1, according to one exemplary embodiment, the wedge members (110) are configured to be mated with the outside walls of the saddle (120). The wedge members (110), as described in greater detail below, are configured with a narrow distal end and wide proximal end. The saddle (120) and the body (130) are configured such that a gap exists between the outer wall of the saddle (120) and the inner wall of the body (130), where the wedge members (110) are to be inserted. The wedge members (110) are configured to be slideably coupled to the saddle (120), and according to one exemplary embodiment, have at least three positions: an initial uncompressed state, a first partially compressed state, and a final fully compressed state. The three states, according to one exemplary embodiment, are described as a level of compression in that when the wedge members (110) are inserted between the saddle (120) and the body (130) the wedge member's narrow distal end is configured to fill the gap between the saddle (120) and the body (130). Upon further insertion the wider portion of the wedge member (110) causes the saddle (120) to be compressed inward. Consequently, by insertion of the wedge members (110), the tulip walls of the saddle (120) are compressed inward compressing the rod (100) within a rod-receiving channel in the saddle (120). The compressive forces are sufficient to lock the rod (100) within the tulip assembly.

According to one exemplary embodiment, as described above, the wedge members (110) are slideably coupled to the outer wall of the saddle (120) through protrusions and slots. According to one exemplary embodiment, the slots and protrusions facilitate in allowing the wedge members (110) to be placed in an initial uncompressed state where the saddle (120) is not compressed at all, a first partially compressed state where the saddle (120) is compressed sufficient to prevent the rod (100) form snapping out of the saddle (120) while still allowing translation of the rod (100) within the assembly, and a final fully compressed state where the saddle (120) is compressed with enough force to fully secure the rod and prevent any movement thereof.

Described above in reference to FIG. 1, several embodiments of the present exemplary system and method have been described. To further understand these and other alternative embodiments, a more detailed description of each element of the system will be described in conjunction with FIGS. 2-10 below.

Figure 2A:
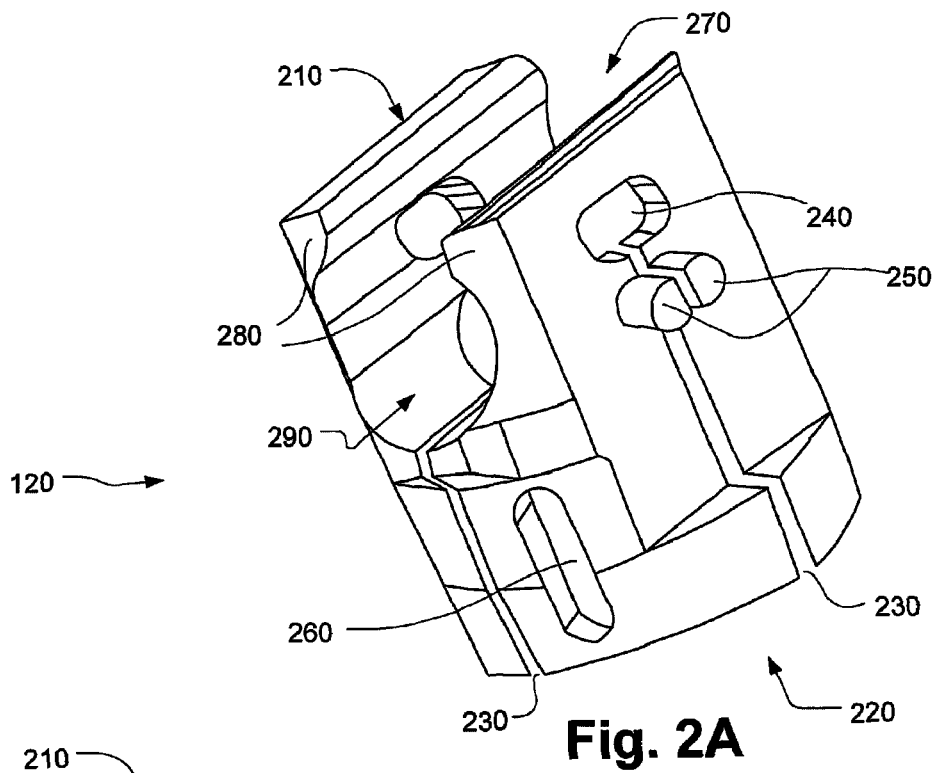
FIGS. 2A and 2B are respectively, a top isometric view and a bottom isometric view of a tulip saddle, according to one exemplary embodiment.
Figure 2B:
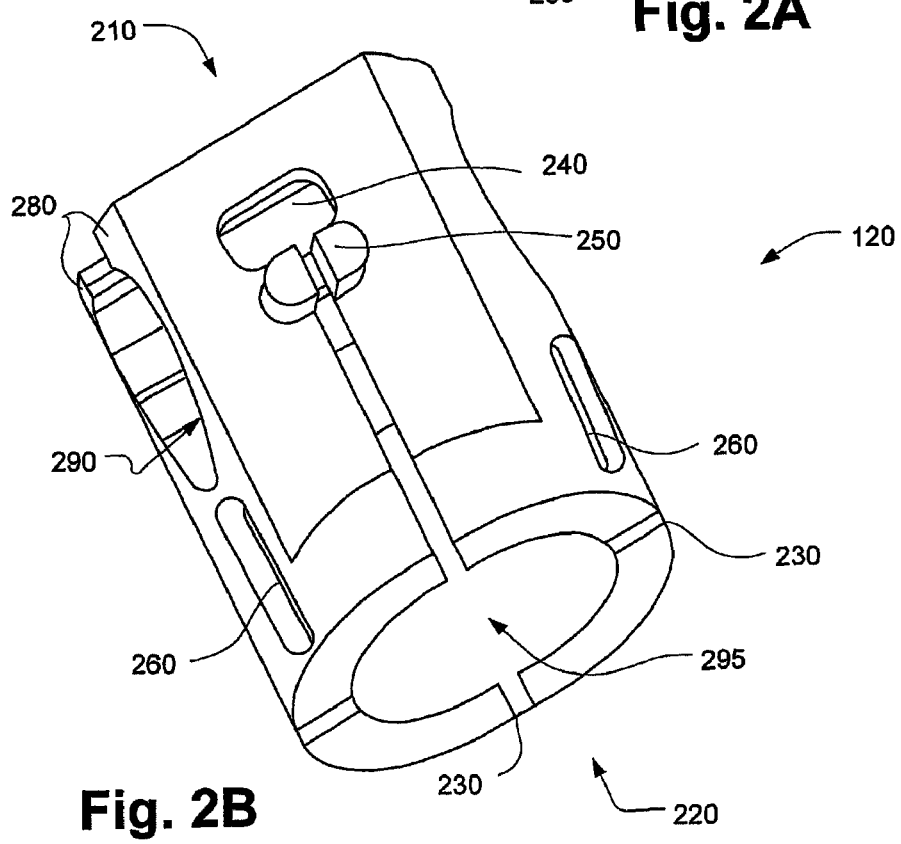

FIGS. 2A and 2B illustrate the tulip saddle (the saddle) (120) through a top isometric view and a bottom isometric view, respectively according to one exemplary embodiment. The saddle (120) as shown in FIG. 2A has a proximal end (210) and a distal end (220). The distal end is configured to receive the head of a pedicle screw and, as illustrated, longitudinal expansion slots (230) allow the distal portion to expand to receive the head portion of a pedicle screw and subsequently contract, thereby capturing the head of the pedicle screw. According to one exemplary embodiment, the longitudinal slots (230) allow the lower portion of the saddle (120) to expand and contract allowing the head of a pedicle screw to be snapped into place; however, according to alternative embodiments, the distal end (220) of the saddle (120) is configured with an orifice allowing the head portion of a pedicle screw to enter wherein an expansion ring is configured to expand and subsequently contract, thereby securing the head of the pedicle screw within the saddle (140).

As illustrated in FIG. 2B, it can be seen that the lower portion near the distal end (220) is configured with an opening (295) through which the head of a pedicle screw enters. The head portion causes the distal end (220) of the saddle (120) to expand with the longitudinal slots (230) facilitating the expansion. Once the head portion has entered at least partially into the orifice (295) the distal end (220) contracts and thereby secures the head of the pedicle screw. Furthermore, according to one exemplary embodiment, expansion reliefs (240) in the walls of the saddle (120) may be provided to allow sufficient expansion of the lower portion.

As illustrated in both FIGS. 2A and 2B, slots (260) are configured in the saddle (120) to receive a pin. The slots, as illustrated, are substantially elongated, however, according to various embodiments, the slots may be of any number of various shapes and sizes. The slots (260) are configured to receive a pin, wherein the pin also passes through corresponding slots on the body (130, FIGS. 1 and 6). With the pin in place through the slots in both the body (130, FIGS. 1 and 6) and the saddle (120, FIG. 2), the saddle (120) is secured to the body. According to one exemplary embodiment, with the pins in place, the saddle (120) and body (130, FIGS. 1 and 6) are slideably coupled, that is, some freedom of movement is allowed. According to one exemplary embodiment, this allows the saddle (120) to be coupled to the head of a pedicle screw while still free to pivot and select a desired angle. Further details of the provisional lock will be provided below.

FIG. 2A also illustrates the rod-receiving channel (270) of the saddle (120). A rod may be snapped within the channel. According to one exemplary embodiment, two protrusions (280) on each side of the channel provide resistance for the rod to enter and exit. Consequently, when a rod is placed within the channel, the protrusions (280) cause the rod to force a slight expansion of the saddle (120). Once the rod is within the channel (290) the saddle (120) contracts again. The rod is effectively snapped in and out of the channel (290).

As previously disclosed, according to one exemplary embodiment, the outer walls of the saddle (120) are substantially flat or planar and are configured to assist in coupling wedge members (110, FIG. 1) to the saddle (110). In other exemplary embodiments, the outer walls of the saddle (120) may be stepped to further enhance or replace the effect of the wedge members (110; FIG. 1). As will be detailed in conjunction with FIG. 3, the saddle (120) is formed with protrusions (250) configured to be mated with the slot in a wedge member (110, FIG. 1).

Figure 3:
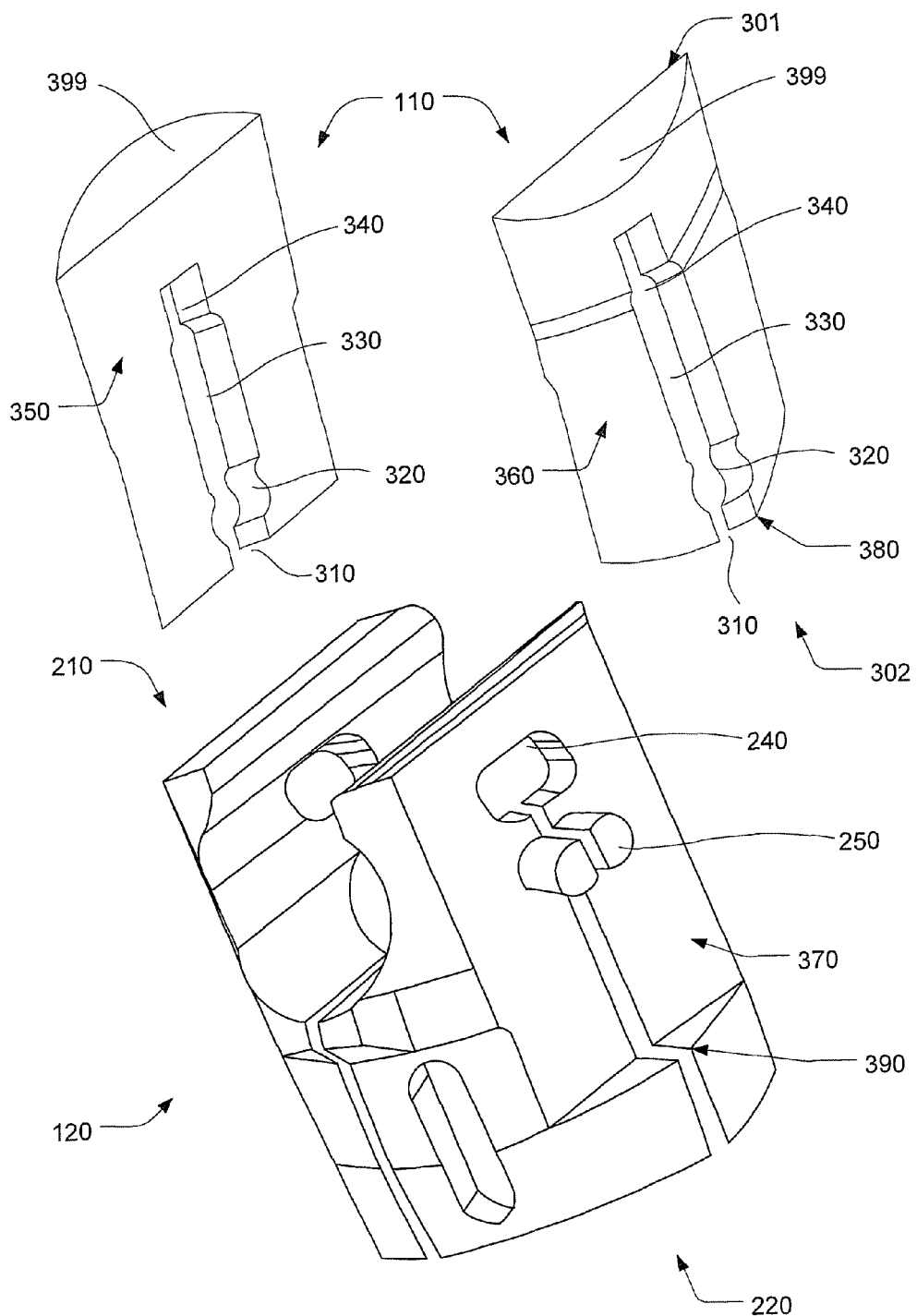
FIG. 3 is an exploded isometric view illustrating wedge members and a tulip saddle, according to one exemplary embodiment.

FIG. 3 further illustrates a tulip saddle (120), according to one exemplary embodiment, and wedge members (110) that are configured to be mated with the saddle (120). As illustrated, the saddle (120) is configured with a flat outer wall (370) that is mated with the flat inner wall (350) of a wedge member (110). The outer wall (360) of the wedge members is substantially rounded and is configured to interact with the inner wall of the body (130, FIGS. 1 and 6). The saddle is further configured with a stop (390); the stop (390) is configured to prevent a wedge member (110) from being inserted further than is desired. Once a wedge member (110) is mated with a saddle (120), the wedge member (110) may continue to be inserted until the distal end (380) of the wedge member (110) encounters the stop (390) on the saddle (120). According to an alternative exemplary embodiment, both the flat outer wall (370) and the flat inner wall (350) may be stepped or tapered to enhance or replace the wedging effect provided by the wedge members, as detailed below.

Furthermore, the saddle (120), as illustrated in FIG. 3, according to one exemplary embodiment, is formed with a protrusion (250) configured to interact with the longitudinal slot (330) in the wedge members (110). The wedge members (110) have a distal end (302) and a proximal end (301). The distal end (302) of the wedge members (110) is relatively thin from the flat inner wall (350) to the rounded outer wall (360), while the proximal end (301) is relatively thick from the inner wall (350) to the outer wall (360). The varying profile of the wedge members (110) creates a wedge shape that upon insertion causes the saddle (120) to compress. According to one exemplary embodiment, the longitudinal slot (330) in the wedge members (110) is configured with a varying profile as illustrated in FIG. 3. The profile of the slot includes, according to one exemplary embodiment, an entrance diameter (310) that is narrower than the width of the protrusions (250) on the saddle, a first position (320) in which the width is substantially identical to that of the protrusions (250), a channel (330) in which the width is substantially identical to that of the protrusions (250). As can be ascertained by FIG. 3, and is shown clearly in FIG. 4, a wedge member (110) has a longitudinal slot (330) configured to be mated with a protrusion (250) of a saddle (120), enabling them to be coupled together in multiple positions.

Figure 4:
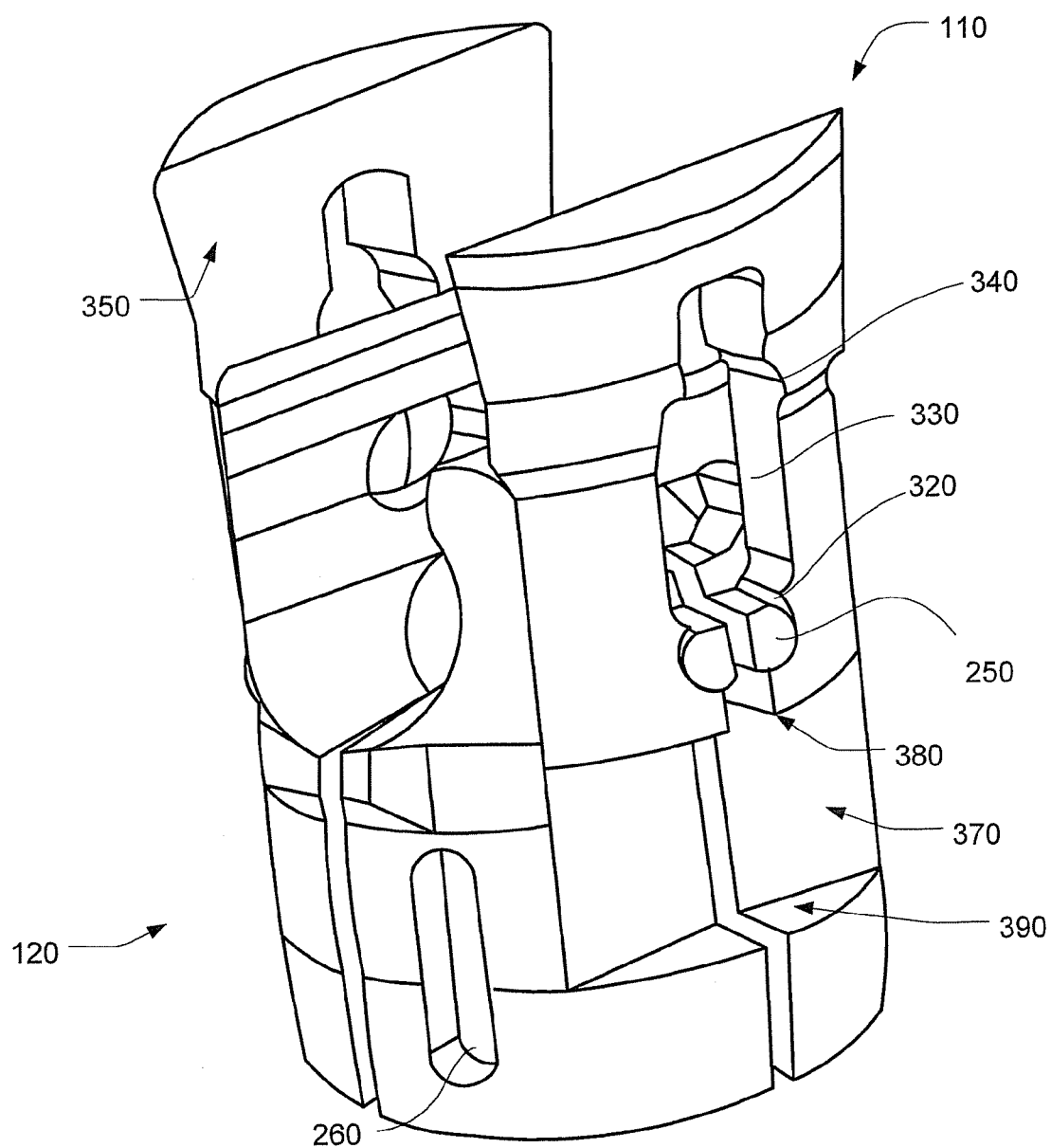
FIG. 4 is an isometric view illustrating two wedge members coupled to a tulip saddle, in a first position, according to one exemplary embodiment.

According to one exemplary embodiment, the wedge members (110) may be coupled to the saddle (120) by the protrusion (250) on the saddle and the slot (330) in the wedge members (110), as illustrated in FIG. 4. According to one exemplary embodiment, the wedge members (110) are configured with a flat or planar side (350) that corresponds to the flat or substantially planar outer wall (370) of the saddle (120). FIG. 4 illustrates the wedge members (110) coupled to the saddle (120). As shown, the protrusion (250) is in the first position (320) of the longitudinal slots (330) of the wedge members (110). It can be seen that the wedge members (110) may be slid further down the side of the saddle (120). When slid down the side of the saddle (120), the protrusions (250) enter the channel (330) and ultimately advance to the final position (340). It can also be seen in FIG. 4 that the lower portion (380) of the wedge members (110) will contact the stop (390) of the saddle (120) as the protrusion (250) enters the final slot position (340).

Figure 5A:
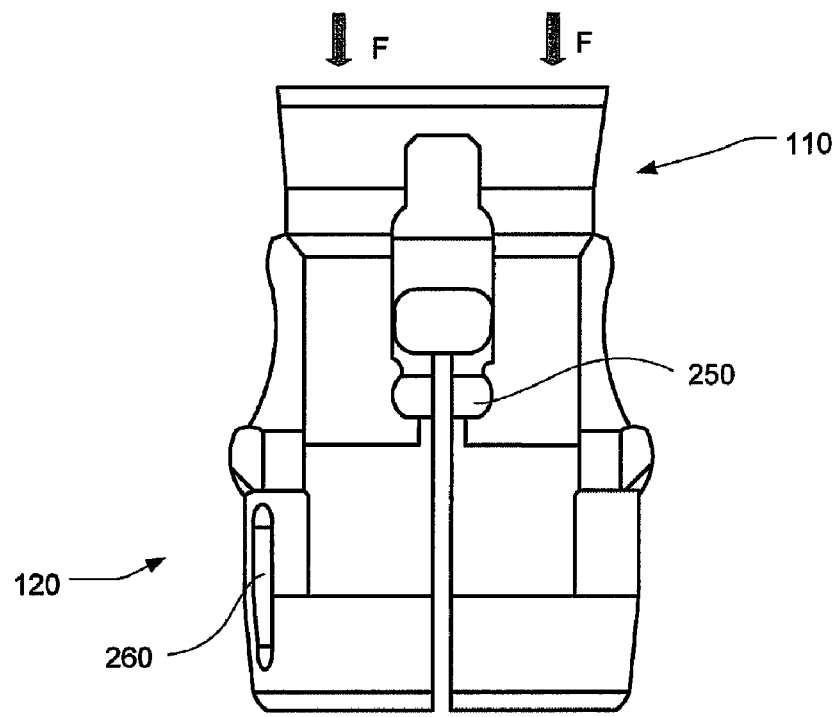
FIGS. 5A and 5B are respectively, side views of a wedge member coupled to a tulip saddle in a first position and a final position, according to one exemplary embodiment.
Figure 5B:
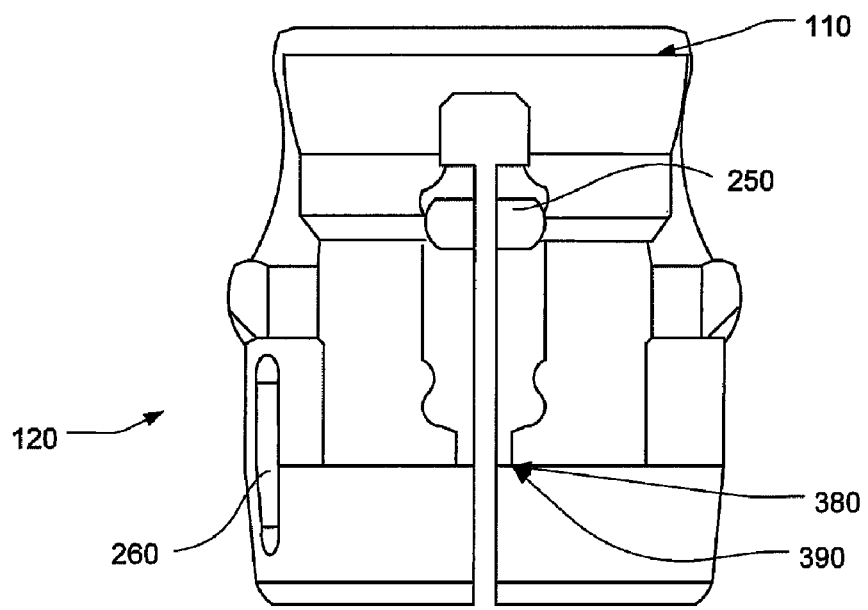

To further elucidate the coupling and sliding action of the wedge members (110) with the saddle (120), FIGS. 5A and 5B are side views of the coupling action. FIG. 5A is a side view showing the connection substantially identical of that shown in FIG. 4, wherein the wedge member (110) is coupled to the saddle (120) with the protrusion (250) of the saddle (120) in the first position (320, FIG. 4) of the wedge member (110). Arrows 'F' are shown in FIG. 5A to illustrate that a downward force on the wedge members (110) will cause the assembly to proceed from that of FIG. 5A to that of FIG. 5B, in which the wedge members (110) are shown fully inserted.

FIG. 5B illustrates the wedge members (110) in a final state, wherein the protrusion (250) of the saddle (120) is in a final position (340, FIG. 4). It is also of note that the lower portion (380) of the wedge members (110) has contacted the stop (390) of the saddle (120). As illustrated in FIG. 5A, the channel (290, FIG. 2) is in a relatively uncompressed state, with the protrusion (250) in the first position (320, FIG. 4). As illustrated in FIG. 5B, the channel (290, FIG. 2) is in a fully compressed state, with the protrusion (250) in a final position (340, FIG. 4). As previously described the channel (290, FIG. 2) may be placed in a partially compressed state by maintaining the protrusion (250) within the longitudinal slot (330) of the wedge members (110) between the first position (320, FIG. 4) and the final position (340, FIG. 4). The compression of the channel (290, FIG. 2) is caused, at least in part, by the wedge members (110) being inserted between the saddle (120) and the body (130, FIGS. 1 and 6) as will be described in greater detail below.

Figure 6:
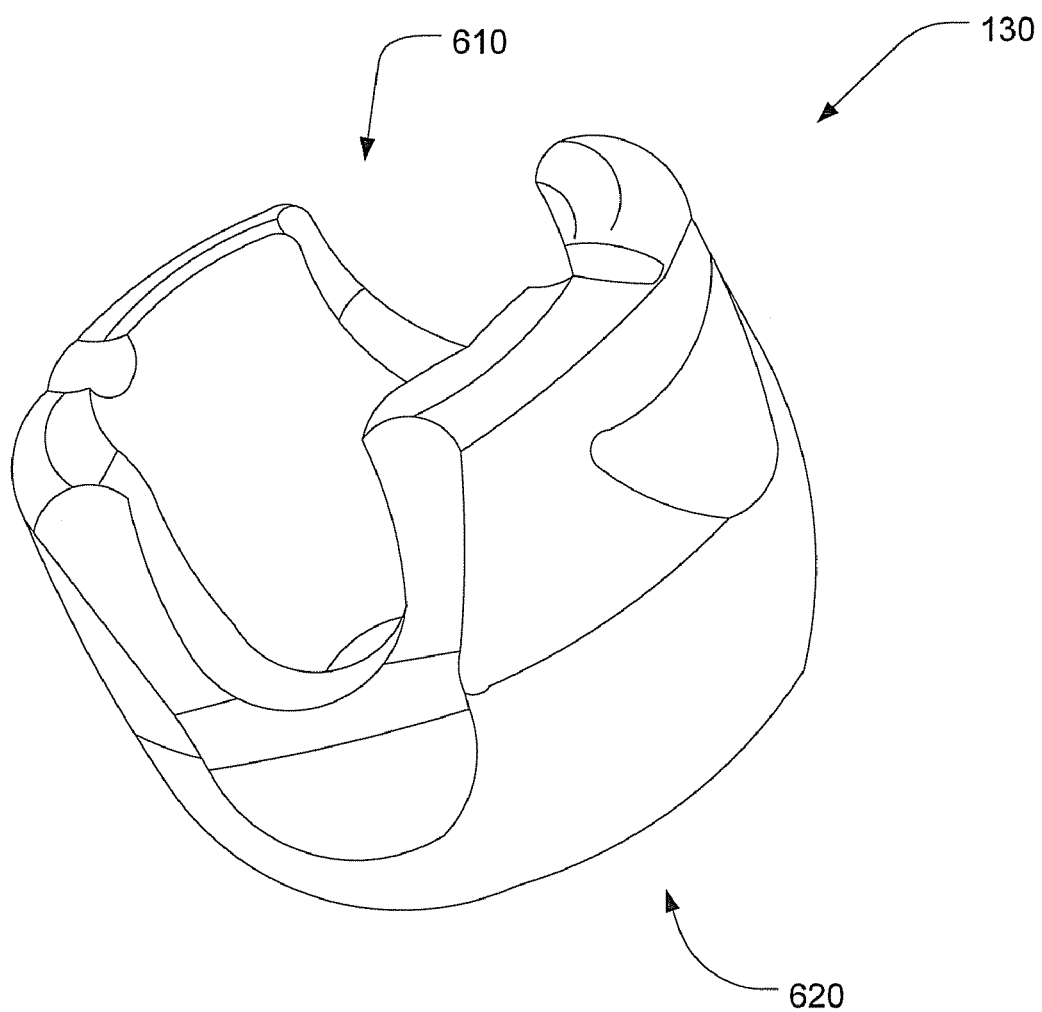
FIG. 6 is an isometric view of a tulip body, according to one exemplary embodiment.

Prior to the details of the interaction of the wedge members (110) and saddle (120) and the body (130), we briefly examine the body (130) as illustrated according to one exemplary embodiment in FIG. 6. The importance of the body is in both the securement of the head of a pedicle screw and the securement of a rod within the tulip assembly. As illustrated, the body (130) is substantially cylindrical with tulip walls defining a channel wherein a rod may be placed. The body (130) has a through bore extending from the proximal end (610) to the distal end (620) configured to receive a saddle (120, FIG. 1). A saddle (120, FIG. 1) may be inserted from the proximal end (610) and subsequently secured to the body (130). The securement of the body (130) to the saddle (120) may be accomplished, according to one exemplary embodiment, by inserting pins through slots (not shown) in the body (130) and into slots (260, FIG. 2) in the saddle (120, FIG. 2). The body is configured with a varying inner diameter, wherein the inner diameter is configured to interact with a saddle to capture and secure the head of a pedicle screw. The manner of interaction between the various features is best described in conjunction with cross sectional views and will be described below.

FIG. 7A is a cross sectional view of a tulip assembly comprising a body (130), a saddle (120), and wedge members (110) prior to attachment of a pedicle screw (140) and insertion of a rod (100), according to one exemplary embodiment. As illustrated in FIG. 7A and the subsequent figures, the tulip assembly is fully constructed prior to attachment to a pedicle screw (140) and prior to insertion of a rod (100), according to one exemplary embodiment. According to alternative embodiments, the order of coupling the saddle (120) to the body (130), coupling the wedge members (110) to the saddle (120), snapping a rod (100) within the channel (290) of the saddle (120), and capturing the head (155) of a pedicle screw (140) may be performed in any order desired.

Returning to FIG. 7A, it can be seen that the saddle (120) has an opening (295) configured to receive the head (155) of a pedicle screw (140). The opening (295) has an entrance diameter (705) smaller than the diameter of the head (155) of the pedicle screw (140). Consequently, when the head (155) is inserted into the opening (295), the entrance diameter (705) of the saddle (120) is forced to expand and receive the head (155). The expansion of the saddle (120) is aided by longitudinal slots (230, FIG. 2) and expansion reliefs (240, FIG. 2) previously described herein. Once the widest diameter of the pedicle screw head (155) has passed the entrance diameter (705), the entrance diameter (705) retracts and the head (155) of the pedicle screw (140) is captured within the opening (295) with the widest diameter of the head (155) corresponding to the middle diameter (710) of the opening (295). According to one exemplary embodiment, the middle diameter (710) is approximately the same diameter as the widest diameter of the head (155) of the pedicle screw (140). However, the middle diameter (710) may be slightly smaller than the widest diameter of the head (155) of the pedicle screw (140) in order to provide some slight friction that may aid in maintaining the relative position of the saddle (120) relative to the pedicle screw prior to locking of the assembly. As used herein, and in the appended claims, the term "approximately as large as," when referring to the diameter of the saddle openings, shall be interpreted as including slight variations between the comparable diameters.

FIG. 7B. illustrates the tulip assembly after the pedicle screw (140) as been successfully snapped into place, according to one exemplary embodiment. It should be noted that in FIGS. 7A-7C, the wedge members (110) are in the first position, wherein the saddle is in a relatively uncompressed state. The first position of the wedge members is described in detail above in reference to FIGS. 5A and 5B. FIG. 7B illustrates the tulip assembly, according to one exemplary embodiment, coupled to a pedicle screw (140) and prepared for reception of a rod (100).

FIG. 7C illustrates the tulip assembly of FIGS. 7A and 7B after a rod (100) has been snapped into place. The rod is snapped into place due to the resistance provided by protrusions (280, FIG. 2) extending inward from the walls of the saddle (120). It should be noted that the rod (100) is free to be snapped in and out of the assembly and may also be translated longitudinally through the channel (290, FIG. 2), as the wedge members (110) are in a first position as in FIG. 5A. According to one exemplary embodiment, the pedicle screw (140) is captured by the tulip assembly in that the head portion (155) is received in the opening (295) of the saddle (120). However, according to one exemplary embodiment, the saddle (120) and the body (130) interact to enable the head to be captured in two states, a first partially secured state in which the tulip assembly may be rotated and pivoted relative to the pedicle screw (140), and a second state in which the tulip assembly is fully secured and the tulip assembly and the pedicle screw (140) are locked at a relative angle and all movement is prevented.

As can be seen in FIG. 7C, according to one exemplary embodiment, the lower portion (720) of the saddle (120) is configured to interact with a lower portion (730) of the inner wall of the body (130). As shown in FIG. 7C, the lower portion (720) of the saddle (120) is not in compressive contact with the lower portion (730) of the body (130). Consequently, the head (155) of the pedicle screw (140) is captured in a partially secured sate as described above. By forcing the saddle (120) further down into the body (130), both the lower portions (720, 730) of the saddle (120) and the body (130) are forced together. The lower portion (730) of the body (130)

causes the lower portion (720) of the saddle (120) to compress the head (155) of the pedicle screw (140) and thereby create and interference fit locking the pedicle screw (140) in place. This can be seen, according to one exemplary embodiment, in FIG. 8.

Figure 8:
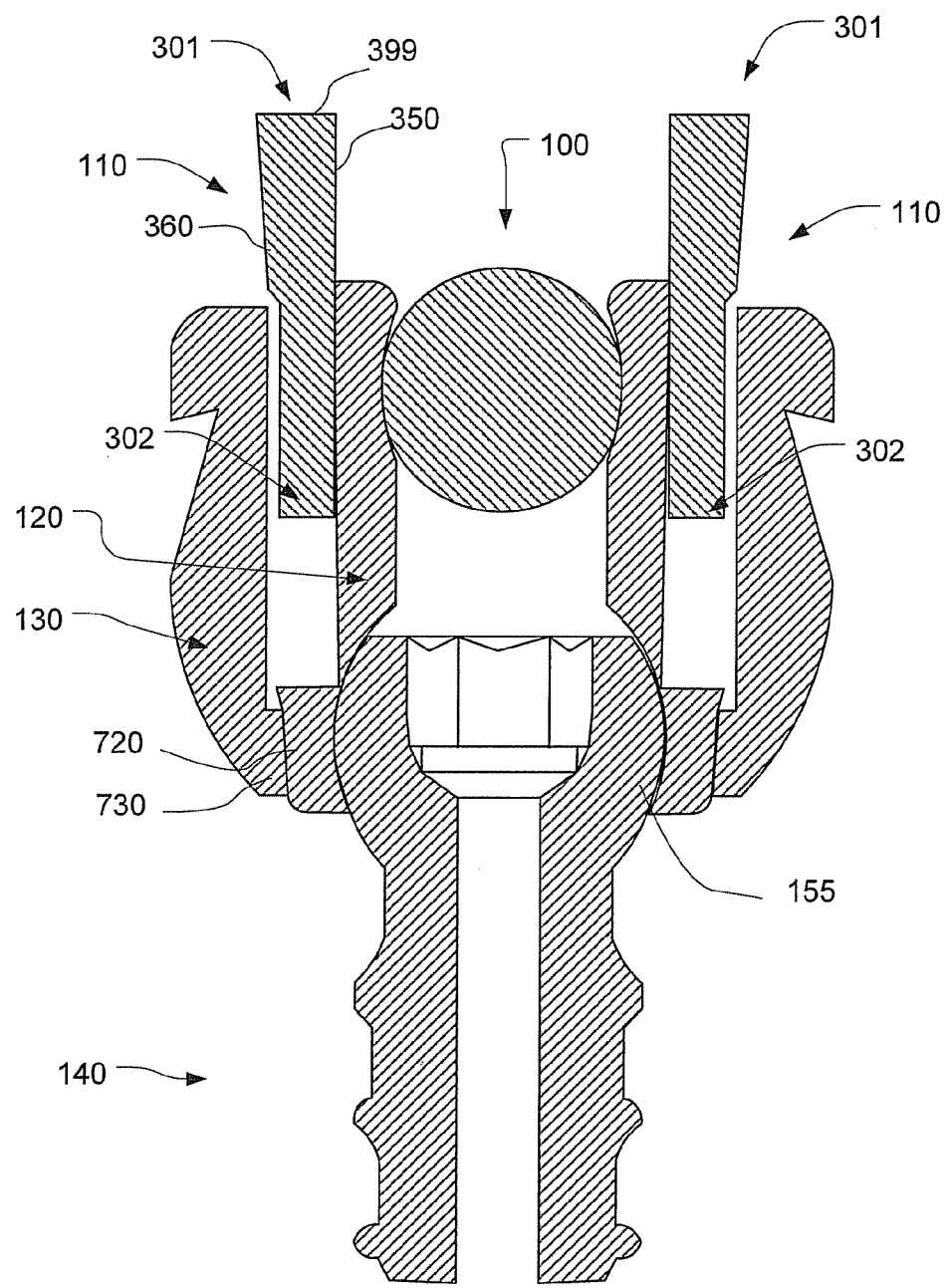
FIG. 8 is a cross sectional view illustrating a tulip assembly coupled to a pedicle screw in a second, fully secured state, and a rod snapped in place in an initial unsecured state, according to one exemplary embodiment.

FIG. 8 is a tulip assembly similar to those of FIGS. 7A-C in that the tulip assembly is fully assembled, a rod (100) is snapped in the channel (290, FIG. 2), and the tulip assembly has captured the head (155) of a pedicle screw (140). FIG. 8 illustrates that the saddle (120) has been forced down fully into the body (130), thereby causing the lower members (720, 730) to contact one another and compress the lower member (720) of the saddle (120). The compressive forces are configured to be sufficient to lock the head (155) of the pedicle screw (140) within the tulip assembly and prevent any motion thereof. It is of note that the wedge members (110) as illustrated in FIG. 8 are in a first position, as described in conjunction with FIG. 5A, in which the rod is free to be snapped in and out or be translated longitudinally.

Figure 9:
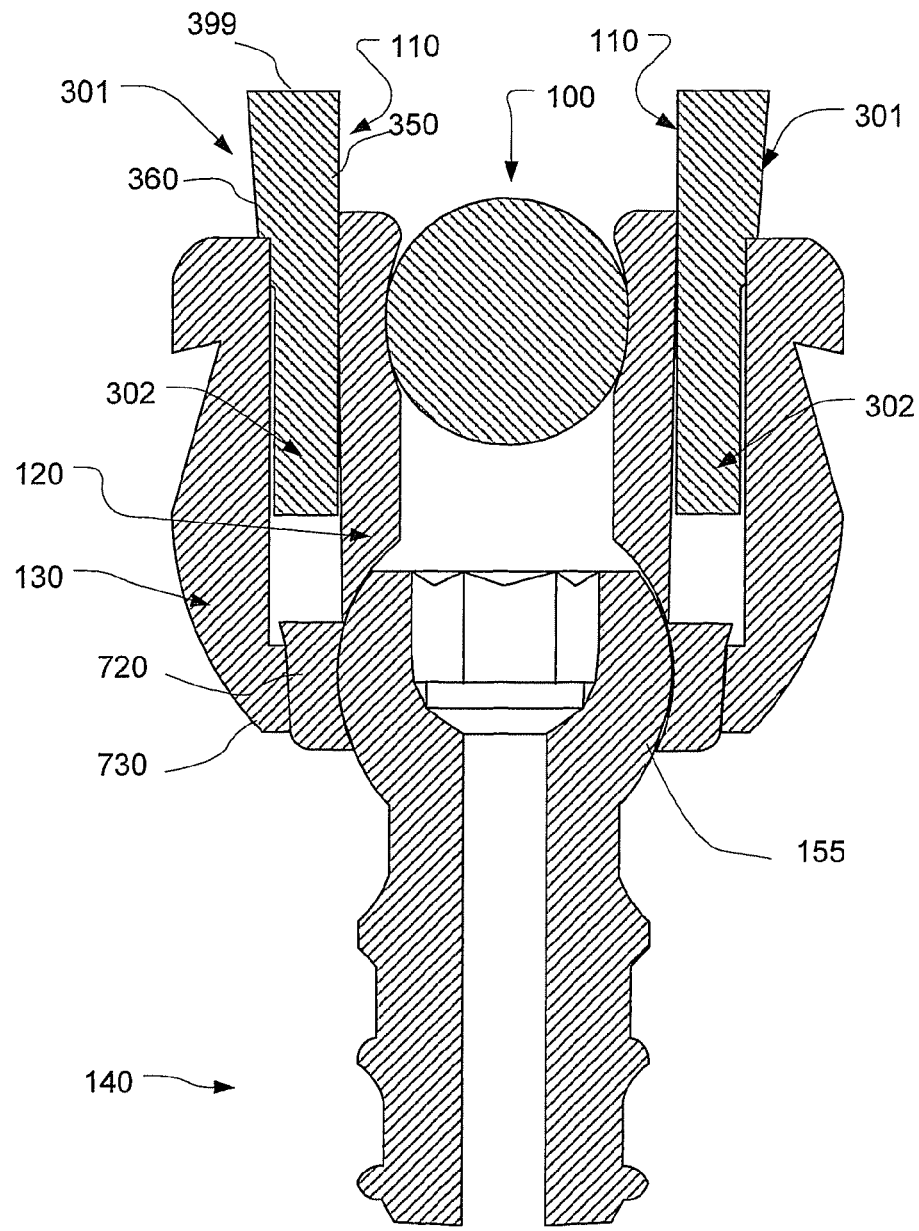
FIG. 9 is a cross sectional view illustrating a tulip assembly fully securing a pedicle screw and a rod in a partially secured state, according to one exemplary embodiment.

FIG. 9 illustrates a tulip assembly, rod (100), and pedicle screw (140) similar to those previously described with the wedge members (110) partially inserted. As previously disclosed and shown in corresponding figures, according to one exemplary embodiment, the wedge members (110) are substantially thicker on the proximal end (301) than on the distal end (302). As illustrated in FIG. 9, the wedge members (110) are coupled to the saddle (120) as described in conjunction with FIG. 4. While the wedge members (110) in FIG. 8 are shown in a first fully uncompressed state, FIG. 9 illustrates the wedge members (110) partially inserted with the thicker proximal end (301) entering the space between the saddle (120) and the body (130). As illustrated in FIG. 9, and previously described, the wedge members (110) are not fully inserted into a final fully compressed state, but are rather in a partially compressive state as described above. The partial insertion of the wedge members (110) cause the walls of the saddle (120) to be compressed inward, resulting in compression of the channel (290, FIG. 2). Consequently, in the partially compressed state of FIG. 9, the channel (290, FIG. 2) is compressed sufficiently to prevent the rod (100) from being snapped out, thereby capturing the rod (100) within the channel (290, FIG. 2). However, according to one exemplary embodiment, the rod illustrated in FIG. 9 is still free to be translated longitudinally within the tulip assembly.

Figure 10:
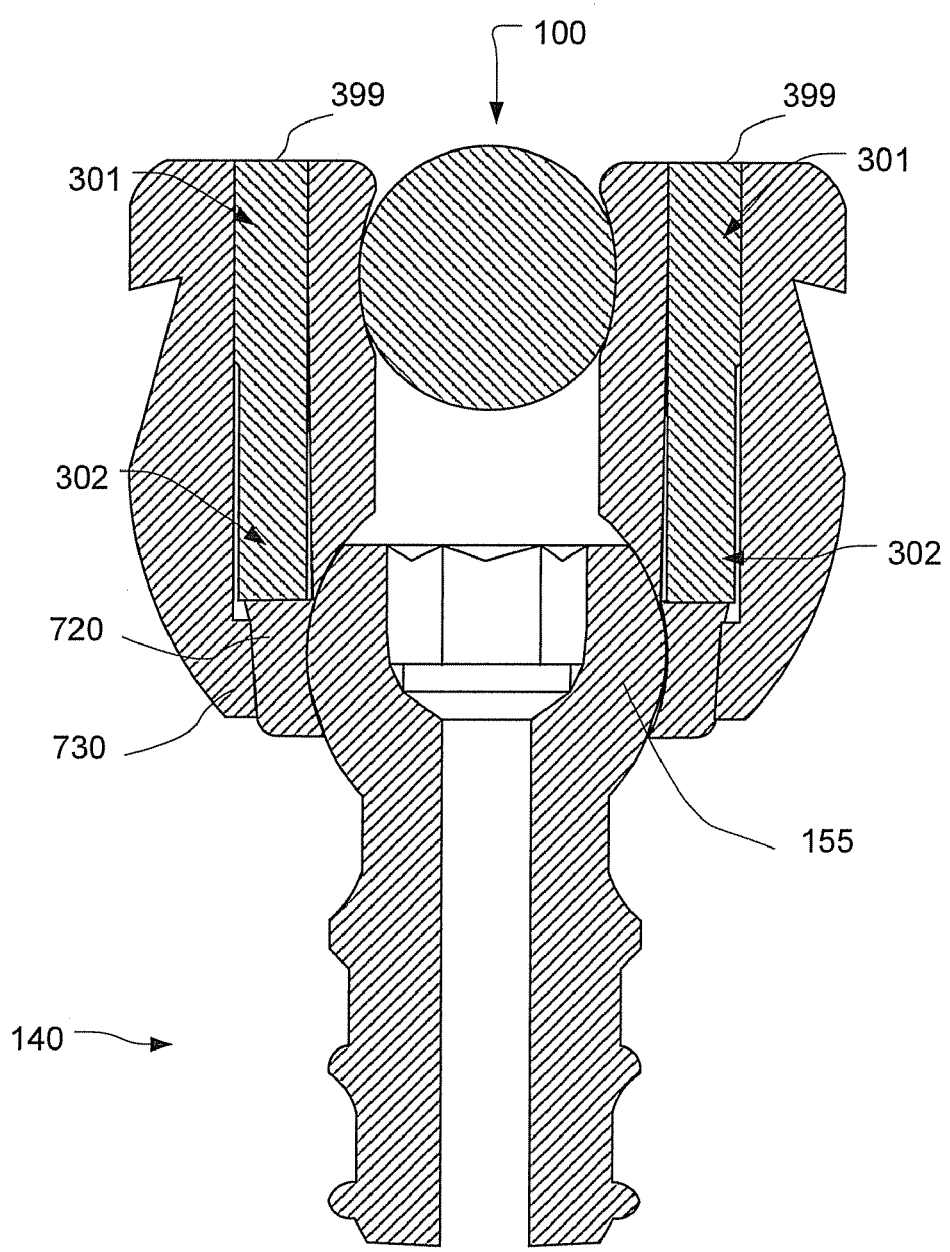
FIG. 10 is a cross sectional view illustrating an assembled tulip assembly coupled to a pedicle screw in a second, fully secured state, and a rod snapped in place in a final fully secured position, according to one exemplary embodiment.

FIG. 10 is a tulip assembly in a fully locked state, according to one exemplary embodiment. As illustrated in FIG. 10, a primary advantage of the system and method herein described is that the resulting tulip assembly in a final locked state has a low profile. While the uppermost portion of the assembly may be functional while assuming any height, depending on the height of the individual components, one exemplary embodiment of the present exemplary system includes an embodiment wherein the uppermost portion of the assembly is parallel with or lower than the uppermost surface the rod (100). FIG. 10 illustrates the wedge members (110) fully inserted and in a final position as described above in conjunction with FIG. 5B. As illustrated, the fully inserted wedge members (110) create an interaction between the relatively wide proximal ends (301) of the wedge members (110) and the walls of the saddle (120), forcing the walls of the saddle (120) inward causing the channel (290, FIG. 2) to be fully compressed. The compressive forces caused by the wedge members (110) are sufficient to cause the rod (100) to be locked in an interference fit within the channel (290, FIG. 2). As illustrated in FIG. 10, the rod (100) is fully locked and is prevented from both snapping out of the channel and from translation within the channel. As previously described, and as shown again in FIG. 10, the saddle (120) has been forced down fully into the body (130). Consequently, the head of the pedicle screw (140) is fully locked within the tulip assembly and all relative movement is prevented. The purpose of the forgoing description and illustrations has been to provide a detailed understanding of the exemplary structure of the system and method herein described, not necessarily the order of the steps necessary to arrive at this final state. For example, it is entirely conceivable, that the rod may be fully secured within the tulip assembly prior to any interaction with a pedicle screw, or vice versa.

Exemplary Method

Figure 11:
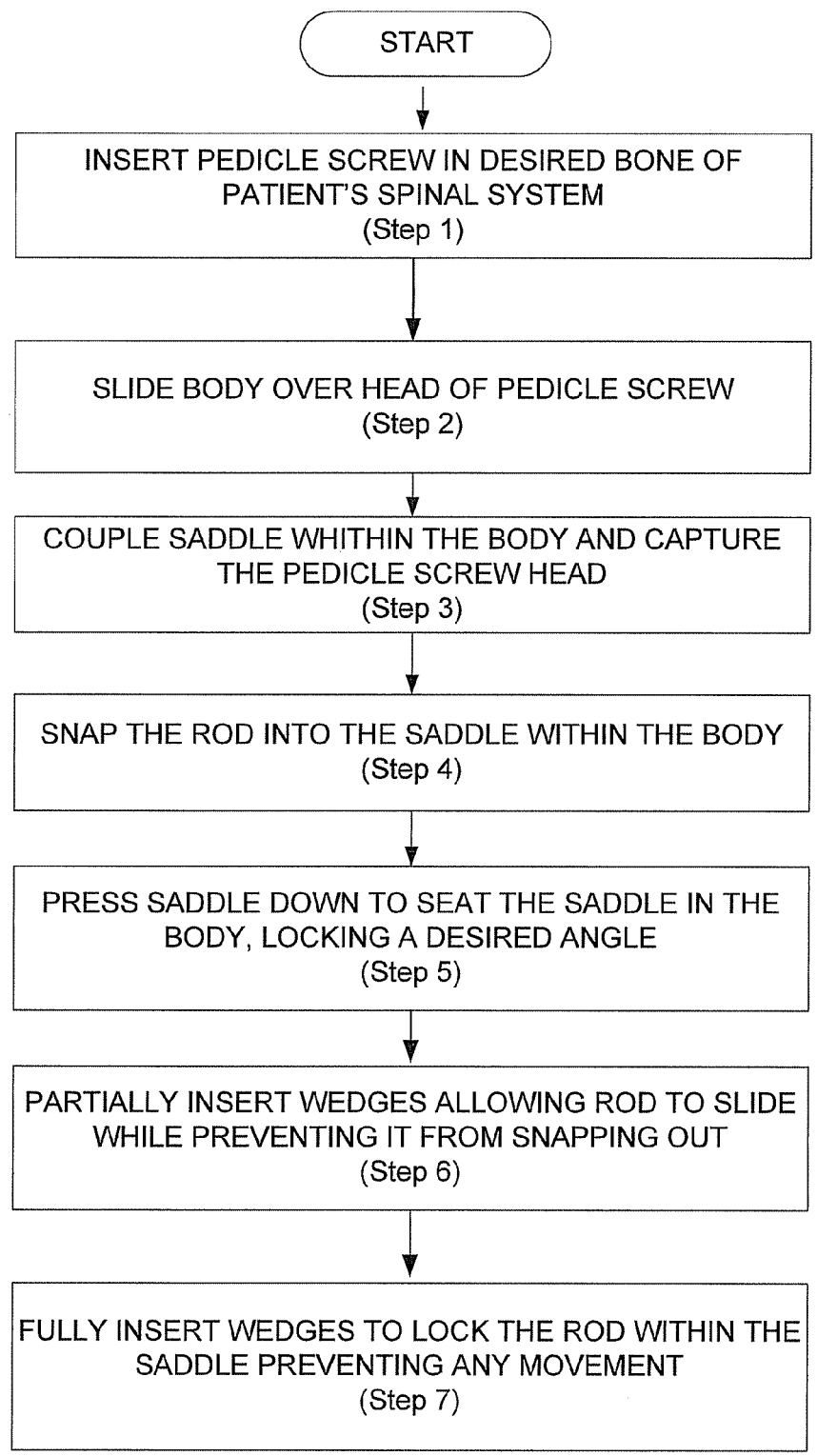
FIG. 11 is a flowchart illustrating a method of installing a pedicle screw and subsequent securing of a rod within the tulip assembly secured to the pedicle screw, according to one exemplary embodiment.

FIG. 11 is a flow chart illustrating an exemplary method for installing a pedicle screw, coupling a tulip assembly, and securing a rod within the tulip assembly, according to one exemplary embodiment. It should be understood that the following description in conjunction with FIG. 11 is provided as an example of a method of use according to one exemplary embodiment and that many modification of the method are possible, including a rearranging of the steps, elimination of steps, or the inclusion of additional intermediate steps, all of which are not only possible, but highly likely. For ease in describing the present exemplary system and method only, the present exemplary method is described in the context of a previously un-assembled tulip member. However, any number of components of the present exemplary system may be pre-assembled prior to insertion into a patient. All numerical references are with respect to FIG. 1 while step references are with respect to FIG. 11, unless otherwise noted.

The insertion of a pedicle screw into a patient's bone (Step 1) for subsequent coupling of a rod is common in medical practice and is well understood in the prior art. Often a bone screw is inserted into one or more vertebrae and rods coupling each bone screw act to support the vertebrae and/or prevent movement thereof. As illustrated in FIG. 1, driving features (145) on the head (155) of a pedicle screw (140) may be utilized to drive the pedicle screw (140) into the patient's bone. However, it is within the scope of this disclosure to use various pedicle screws, bone screws, or other anchoring devices as deemed appropriate.

Following insertion of a bone screw (Step 1), the tulip body (130) may be positioned over the head (155) of the bone screw (140) by passing the head (155) through the bore (Step 2). As described in Step 3 (Step 3) the saddle (120) may be coupled to the body (130) and the head (155) of the pedicle screw may be captured within the saddle (130). According to an alternative embodiment, the saddle (120) and the body (130) may be coupled first and then snapped onto the head (155) of a pedicle screw (140). Or, according to yet another embodiment, the saddle (120) and the body (130) may be manufactured as a single element, wherein a portion of the single element is configured to be slidable with respect to the other portion and perform the functions of the saddle (120) described herein.

With the pedicle screw (140) installed (Step 1) and the body (130) and saddle (120) coupled and secured (Steps 2 and 3), at least partially, to the pedicle screw (140), a rod (100) may be snapped (Step 4) into the channel (290, FIG. 2) of the saddle (120). As described herein and as shown in FIG. 11 the rod (100) is snapped into place prior to the wedge members (110) being placed and coupled to the saddle (120), according to one exemplary embodiment.

The saddle (120) may have initially been coupled to the body (130) to partially capture the head (155) of the pedicle screw (140), as described in Step 3. By pressing down on the saddle (120) and/or by pulling up on the body (130), lower portions (720, 730) of both the saddle and body interact to cause the lower portion (720) of the saddle (120) to compress the head of the pedicle screw sufficient to lock a relative angle (Step 5) between the tulip assembly and the pedicle screw (140). It is of note that all of the figures illustrate the tulip assembly and the pedicle screw (140) as having no relative angle, this is according to one manner of placement. Alternatively, a surgeon may choose to orient the tulip assembly to any desired angle relative to the pedicle screw prior to fully locking an angle.

Inserting the wedge members (110) into a first uncompressed state will not secure the rod. Consequently, insertion of the wedge members (110) may be performed in situ or prior to insertion at any time prior to Step 6. With the wedge members (110) coupled to the saddle (120), a downward force on the wedge members (110) will cause them to enter partially between the saddle (120) and the body (130). This will, as described above, cause a force on the walls of the saddle (120) to compress the channel (290, FIG. 2) and thereby create an interference fit with the rod (100). As previously described, by only partially inserting the wedge members (110), the channel (290, FIG. 2) is compressed sufficiently to prevent the rod (100) from snapping out, while still allowing the rod (100) to translate longitudinally within the channel.

With the tulip assembly fully secured to a pedicle screw (140) and wedge members (110) partially inserted causing the rod (100) to be captured while still allowing longitudinal movement, the rod (100) may be fully locked within the tulip assembly by forcing the wedge members (110) down completely (Step 7). After completely locking the rod (100) and fully securing the pedicle screw (140), the complete assembly is described as a low profile pedicle screw assembly because the upper most portions of the tulip assembly are parallel with or lower than the upper most portion of the rod (100).

FIGS. 12A-F provide an illustration of the foregoing exemplary method. The figures are intended to represent one exemplary method, as such it should be understood that the order may be modified or steps may be combined, omitted, or added as deemed necessary without straying from the spirit of the exemplary method. FIGS. 12A-F are, according to various exemplary embodiments, alternative embodiments described and those modifications that may be obvious due to the teachings and disclosures provided herein may not be fully represented by the figures. FIG. 12A illustrates the tulip assembly comprising two wedge members (110), a saddle (120), and a body (130) coupled to one another prior to securement of a screw head (155) and prior to the capture of a rod (100).

FIG. 12B illustrates the initial capture of the head of a screw. As illustrated, the pedicle screw (140) is captured within the saddle (120). However, the saddle (120) is free to pivot around the head, as it has not been fully locked, corresponding to Step 3 of FIG. 11. FIG. 12C illustrates the subsequent capture of a rod (100), according to one exemplary embodiment. As can be seen in FIG. 12C, the rod (100) effectively snaps into the channel (290, FIG. 7A), corresponding to Step 4 of FIG. 11.

FIG. 12D illustrates the fully locked head of a screw (140) within the saddle (120). As shown the tulip assembly is locked with no relative angle; however, as previously disclosed the tulip assembly may be locked at a desired angle relative to the screw (140). FIG. 12D corresponds to Step 5 of FIG. 11. FIG. 12E illustrates the wedge members (110) partially inserted, wherein the insertion is to the point of partially locking a rod (100) within the saddle (120). That is, the rod (100) is prevented from snapping out, while still free to translate longitudinally. FIG. 12E corresponds to Step 6 of FIG. 11.

FIG. 12F illustrates the wedge members (110) fully inserted. This is an illustration of the completely installed system, according to one exemplary embodiment. As illustrated, the uppermost portion of the assembly is the rod (100) itself. This allows for a low profile system, advantageous in MIS techniques. The rod (100) is fully secured within the saddle and the tulip assembly is fully secured to the head of the screw (140), corresponding to Step 7 of FIG. 11.

According to one exemplary embodiment, various members of the tulip assembly may be anodized, painted, varied in surface finish, or in other manners common in the art configured with various colors. According to one embodiment, by coloring various members of the tulip assembly or even various faces of the members of the tulip assembly, a person installing the system would be able to visually ascertain the state of securement the system is in by which colors are viewable.

As an example of how this may be preformed, the following is a description of the usefulness of coloring, exemplified by coloring the wedge members. Referring to FIG. 3, the top most face (399) of the wedge members (110) might be colored, for example silver, the same as the other portions of the tulip assembly including the body (FIG. 6, 130) and the saddle (FIG. 3, 120), while the flat inner face (350) and the rounded outer face (360) might be colored a distinct color from the rest of the system, for example blue. Consequently, when the wedge members (110) are inserted in a first initial state, as shown in FIG. 8, a majority of the system would be silver. However, both the flat inner face (350) and the rounded outer face (360) of both wedge members (110) would display a distinct blue color, alerting the surgeon that the system is not in a fully secured state.

Upon further insertion, to the point the wedge members (110) are fully inserted as shown in FIG. 10, the flat inner face (350) and the rounded outer face (360) of the wedge members (110) are within the tulip assembly and are not visible to the surgeon. Only the upper face (399) that is colored silver, similar to the other portions of the tulip assembly, is visible; consequently when the wedge members are fully inserted as in FIG. 10, and the system is in a fully secured state, only the color silver will be visible, the lack of the color blue would indicate that the system is fully locked.

According to another alternative embodiment, the wedge members (110) may include a top face (399) colored one color, for example silver; the top half of the wedge members (110) on both the inner flat face (350) and the outer rounded face (360) colored another color, for example blue; and the bottom half of the wedge members (110) on both the inner flat face (350) and the outer rounded face (360) colored a third color, for example red; where the other portions of the tulip assembly are neither red nor blue. According to this exemplary embodiment, if the wedge members (110) are in an initial uncompressed state, as in FIG. 8, the surgeon will see both red and blue, indicating that the system is completely unsecured. With the wedge members (110) in a partially secured state, as in FIG. 9, the surgeon will see only blue, indicating that the system is partially secured. With the wedge members in a final state, as in FIG. 10, the surgeon will see neither red nor blue, indicating that the system is fully secured.

Additionally, according to various embodiments, the interior surface of the saddle (120) is contoured in order to apply high compression forces on both the rod (100) and the head (155) of the pedicle screw (140) ensuring that all members are retained in a fixed position. Of course, the amount of compression and the relative location of the compression can be selected according to desired design by selection of the shape, taper, and relative contour of the interior of the body (130) or the exterior surfaces of the saddle (120) relative to each other and also the contour of the wedge members (110).

Returning briefly to FIG. 10, a cross sectional view of a completed pedicle screw (140), tulip assembly, and rod (100) is depicted. As can be seen in FIG. 10, the top of the body (130), the saddle (120) and the wedge members (110) are pressed downward until the top surfaces are flush with or even slightly recessed below the top surface of the rod (100).

As can be seen in FIG. 10, the uppermost portion of the rod (100) is approximately adjacent to the uppermost portion of the tulip assembly. In one embodiment, the uppermost portions are approximately equal to each other. In alternative embodiments, the uppermost portion of the tulip assembly may be slightly lower so that the rod (100) is somewhat higher.

In conclusion, the present exemplary pedicle screw systems and methods provide a number of exemplary connection members and methods that can be used for percutaneous screw placement. Specifically, the present exemplary systems and methods provide for a low profile pedicle screw and tulip assembly that limits the size of the tulip and eliminates a need for a cap or other top structure. Furthermore, according to one exemplary embodiment, the assembly can be configured such that the tulip is even with or lower than the top of the rod when fully locked. The resulting low profile of the present exemplary pedicle screw and tulip assembly results in less tissue damage and irritation in and around the surgical site, when compared to traditional systems.

It will be understood that various modifications may be made without departing from the spirit and scope of the present exemplary systems and methods. For example, while the exemplary implementations have been described and shown using screws to anchor into bony structures, the scope of the present exemplary system and methods is not so limited. Any means of anchoring can be used, such as a cam, screw, staple, nail, pin, or hook.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A pedicle screw assembly comprising: a screw having a threaded portion and a head portion; a tulip body configured to be positioned on said head portion of said screw; a tulip saddle configured to be coupled to said tulip body within said tulip body; at least one wedge member configured to be inserted between said tulip saddle and said tulip body so that proximal ends of said at least one wedge member, said tulip saddle, and said tulip body are substantially coplanar; wherein said tulip saddle has an upper portion and a lower portion; said lower portion of said tulip saddle being in contact with said tulip body and configured to retain said tulip saddle on said head portion; and said upper portion of said tulip saddle being configured to retain a rod.

2. The pedicle screw assembly of claim 1, wherein said upper portion of said tulip saddle is configured to dispose the uppermost portion of said rod further from said head portion of said screw than any other portion of said tulip saddle, said tulip body, and said at least one wedge member.

3. The pedicle screw assembly of claim 1 wherein said lower portion of said tulip saddle configured to retain said tulip saddle on said head portion comprises: a first diameter smaller than a largest diameter of said head portion; a second diameter approximately as large as a largest diameter of said head portion; wherein when said head portion is forced into said lower portion, said first diameter is configured to expand to receive said head portion; and upon said largest diameter of said head passing through said first diameter, said first diameter contracts to secure said tulip saddle on said head portion.

4. The pedicle screw assembly of claim 3 wherein: said tulip saddle is configured to be coupled to said tulip body in a first position and a second position; wherein said first position includes said lower portion retaining said tulip saddle on said head portion in a partially secured state, wherein said tulip saddle is free to pivot about said head portion while fully retained to said head portion; wherein said second position includes said lower portion retaining said tulip saddle on said head portion in a fully secured state, wherein said tulip saddle is fully locked to said head portion and secures a relative angle between the tulip saddle and said pedicle screw; and wherein said pedicle screw assembly is configured to translate from said first position to said second position by positioning said tulip saddle into said tulip body.

5. The pedicle screw assembly of claim 1 wherein: said upper portion of said tulip saddle comprises an upper entry diameter that is smaller than a diameter of said rod, and a middle rod retaining diameter that is as large as said diameter of said rod; wherein said upper entry diameter is configured to expand to receive said rod upon the application of a force to allow said rod to pass into said middle rod retaining diameter; wherein once said rod has passed into said middle rod retaining diameter, said upper entry diameter returns to said upper entry diameter that is smaller than a diameter of said rod.

6. The pedicle screw of claim 1 wherein said tulip saddle further comprises: at least one outer wall including a wedge coupling protrusion, wherein said at least one wedge member includes a slot configured to receive said wedge coupling protrusion.

7. The pedicle screw of claim 6, wherein said at least one wedge member further comprises: a varying profile; wherein said wedge member is configured to slide between said tulip body and said tulip saddle; wherein said wedge member has an initial width equal to or slightly smaller than a width of a gap between said tulip saddle and said tulip body; and wherein said wedge member has a final width larger than said gap.

8. The pedicle screw assembly according to claim 6, wherein said slot of said wedge member is configured to retain said protrusion in at least three locations; wherein retention of said protrusion in said first location is configured to cause no compression on said upper portion of said tulip saddle; wherein retention of said protrusion in said second location is configured to compress said upper portion of said tulip saddle sufficient to compress said rod within said upper portion while still allowing said rod to be translated longitudinally within said upper portion; and wherein retention of said protrusion in said third location is configured to compresses said upper portion of said tulip saddle sufficient to lock said rod within said upper portion.

9. The pedicle screw of claim 1, wherein said lower portion includes a stop positioned between said tulip body and said head portion of said screw, a distal end of said at least one wedge member being selectively positioned in contact with said stop to limit distal advancement of said at least one wedge member.

10. The pedicle screw assembly of claim 1 wherein said tulip saddle is configured to be coupled to said tulip body in a first position and a second position; wherein said first position includes said lower portion retaining said tulip saddle on said head portion in a partially secured state, wherein said tulip saddle is free to pivot about said head portion while fully retained to said head portion; wherein said second position includes said lower portion retaining said tulip saddle on said head portion in a fully secured state, wherein said tulip saddle is fully locked to said head portion and secures a relative angle between the tulip saddle and said pedicle screw; and wherein when said pedicle screw assembly is in said second position the proximal ends of the at least one wedge member, said tulip saddle and said tulip body are substantially coplanar.

11. A pedicle screw assembly comprising: a screw having a threaded portion and a head portion; a tulip body configured to be positioned on said head portion of said screw; a tulip saddle configured to be coupled to said tulip body within said tulip body; at least one wedge member configured to be inserted between said tulip saddle and said tulip body; wherein said tulip saddle has an upper portion and a lower portion; said lower portion of said tulip saddle being configured to retain said tulip saddle on said head portion; and said upper portion of said tulip saddle being configured to retain a rod;
wherein said tulip saddle further comprises: at least one outer wall including a wedge coupling protrusion, wherein said at least one wedge member includes a slot configured to receive said wedge coupling protrusion;
wherein said slot of said wedge member is configured to retain said protrusion in at least three locations; wherein retention of said protrusion in said first location is configured to cause no compression on said upper portion of said tulip saddle; wherein retention of said protrusion in said second location is configured to compress said upper portion of said tulip saddle sufficient to compress said rod within said upper portion while still allowing said rod to be translated longitudinally within said upper portion; and wherein retention of said protrusion in said third location is configured to compress said upper portion of said tulip saddle sufficient to lock said rod within said upper portion;
wherein said wedge member comprises at least two colors; wherein when said wedge member is in said first state all of said at least two colors are visible; and wherein when said wedge member is in said third state only one of said colors is visible.

12. The pedicle screw assembly of claim 11, wherein said wedge member is colored with at least three colors, wherein when said wedge member is in said second state, only two of said three colors is visible.

13. A pedicle screw and rod assembly comprising: a screw having a threaded portion and a head portion; a tulip body configured to be positioned on said head portion of said screw; a tulip saddle configured to be coupled to said tulip body within said tulip body; at least one wedge member configured to be inserted between said tulip saddle and said tulip body, said at least one wedge member including a proximal end and a distal end; wherein said tulip saddle has an upper portion and a lower portion; said lower portion of said tulip saddle being in contact with said tulip body and configured to retain said tulip saddle on said head portion and said upper portion of said tulip saddle being configured to retain a rod; wherein said tulip saddle further comprises an outer wall including at least one protrusion configured to couple said at least one wedge member to said tulip saddle, said at least one wedge member having a varying profile from a thinner end to a thicker end and a slot configured to receive said protrusion; wherein said at least one wedge member is configured to slide between said tulip body and said tulip saddle; and wherein said upper portion of said tulip saddle is configured to dispose an uppermost portion of said rod further from said head portion of said screw than any other portion of said tulip saddle, said tulip body, and said wedge members.

14. The pedicle screw and rod assembly of claim 13, wherein said at least one wedge member comprises: a distal thickness defining a distal end of said at least one wedge member, wherein said distal thickness is at least as small as a gap between said tulip saddle and said tulip body; and a proximal thickness defining a proximal end of said at least one wedge member, wherein said proximal thickness is larger than said gap between said tulip saddle and said tulip body.

15. The pedicle screw assembly according to claim 14 wherein said slot of said at least one wedge member is configured to retain said protrusion in at least three locations;
wherein retention of said protrusion in said first location is configured to cause no compression on said upper portion of said tulip saddle; wherein retention of said protrusion in said second location is configured to compress said upper portion of said tulip saddle sufficient to compress said rod within said upper portion, while still allowing said rod to be translated longitudinally within said upper portion; and wherein retention of said protrusion in said third location is configured to compress said upper portion of said tulip saddle sufficient to lock said rod within said upper portion.

16. The pedicle screw assembly of claim 13, wherein said lower portion of said tulip saddle configured to retain said tulip saddle on said head portion comprises: a first diameter smaller than the largest diameter of said head portion; a second diameter at least as the largest diameter of said head portion; wherein when said head portion is forced into said lower portion, said first diameter is configured to expand to receive said head portion; and upon said largest diameter of said head passing through said first diameter, said first diameter contracts to secure said tulip saddle on said head portion.

17. The pedicle screw assembly of claim 16, wherein said lower portion of said tulip saddle further comprises expansion slots.

18. The pedicle screw assembly of claim 17 wherein said tulip saddle is configured to be coupled to said tulip body in a first position and a second position; wherein said first position includes said lower portion retaining said tulip saddle on said head portion in a partially secured state, wherein said tulip saddle is free to pivot about said head portion while fully retained to said head portion; wherein said second position includes said lower portion retaining said tulip saddle on said head portion in a fully secured state, wherein said tulip saddle is fully locked to said head portion and secures a relative angle between the tulip saddle and said pedicle screw; and wherein said pedicle screw assembly is configured to translate from said first position to said second position by positioning said tulip saddle into said tulip body.

19. The pedicle screw assembly of claim 18 wherein said upper portion of said tulip saddle comprises an upper entry diameter that is smaller than a diameter of said rod, and a middle rod retaining diameter that is as large as said diameter of said rod; wherein said upper entry diameter is configured to expand to receive said rod upon the application of a force to allow said rod to pass into said middle rod retaining diameter; wherein once said rod has passed into said middle rod retaining diameter, said upper entry diameter returns to said upper entry diameter that is smaller than a diameter of said rod.

20. A method of connecting a rod to a pedicle screw assembly, comprising: threading a screw having a head into a bone; coupling a tulip saddle to said head of said screw in a first partially secured state; placing a rod into an upper portion of said tulip saddle; inserting at least one wedge member between a tulip body and said tulip saddle in a first position so that only a lower portion of said tulip saddle remains in contact with said tulip body, wherein said first position does not compress said upper portion of said tulip saddle; wherein a top surface of said rod is at least as high as a top surface of each of said tulip saddle, said tulip, and said wedge member when said pedicle screw assembly is fully assembled.

21. The method according to claim 20, further comprising: forcing said tulip saddle from said first partially secured state into a second state, wherein said second state is configured to cause said tulip saddle to retain said head of said screw in a second fully secured state; said lower portion of said tulip saddle being configured to retain said head; wherein said lower portion of said tulip saddle includes a first diameter smaller than the largest diameter of said head; and wherein said lower portion of said tulip saddle includes a second diameter, said second diameter being as large as said largest diameter of said head; wherein when said head portion is forced into said lower portion, said first diameter is configured to expand to receive said head portion; and upon said largest diameter of said head passing through said first diameter, said first diameter contracts to secure said tulip saddle on said head portion; wherein said lower portion of said saddle includes at least one expansion slot.

22. The method according to claim 21, further comprising: orienting said tulip body and said tulip saddle at a desired angle relative to said screw prior to forcing said tulip saddle from said first position into said second position to secure said tulip saddle at said desired angle relative to said screw.

23. The method according to claim 22 wherein placing said rod within said upper portion of said tulip saddle comprises: forcing the rod past an upper entry diameter of said upper portion and into a middle rod retaining diameter, wherein said upper entry diameter of said upper portion is smaller than a diameter of said rod, and wherein said middle rod retaining diameter has a diameter substantially equal to a diameter of said rod; wherein said upper entry diameter expands as said rod passes and contracts once said rod has passed into said middle rod retaining diameter.

24. The method according to claim 23, further comprising: inserting said at least one wedge member between said tulip body and said tulip saddle into a second position; wherein said second position causes said at least one wedge member to compress said tulip saddle sufficient to prevent said rod from passing through said upper entry diameter, while still allowing said rod to be translated longitudinally within said middle rod retaining diameter.

25. The method according to claim 24, further comprising: inserting said at least one wedge member between said tulip body and said tulip saddle into a final position; wherein said final position causes said at least one wedge member to compress said tulip saddle sufficient to lock said rod within said saddle and prevent any movement of said pedicle screw assembly.

* * * * *